United States Patent [19]

Brown

[11] Patent Number: 5,567,849
[45] Date of Patent: Oct. 22, 1996

[54] BORANE-SULFIDE HYDROBORATION AGENTS

[75] Inventor: Herbert C. Brown, West Lafayette, Ind.

[73] Assignee: Aldrich Chemical Company, Inc., Milwaukee, Wis.

[21] Appl. No.: 437,582

[22] Filed: May 9, 1995

[51] Int. Cl.$^6$ .................... C07F 5/02; C01B 6/10
[52] U.S. Cl. .................... 568/6; 568/18; 568/75
[58] Field of Search .................... 568/6, 18, 75

[56] References Cited

U.S. PATENT DOCUMENTS

| | | | |
|---|---|---|---|
| 3,378,344 | 4/1968 | Horn et al. | 568/6 |
| 3,882,037 | 5/1975 | Brown | 568/6 |
| 4,298,750 | 11/1981 | Brown | 568/6 |

OTHER PUBLICATIONS

Coyle et al, J.A.C.S, vol. 84, pp. 2989–2994 (1959).

Primary Examiner—James H. Reamer
Attorney, Agent, or Firm—Niblack & Niblack, P.

[57] ABSTRACT

A borane-sulfide represented by the formula $$BH_3 \cdot SR^1R^2$$

wherein B is boron, H is hydrogen, $R^1$ and $R^2$ each are straight or branched chain alkyl or alkoxy with at least one R being a branched chain when both $R^1$ and $R^2$ are alkyl, and S is sulfur. The compounds are hydroboration agents.

13 Claims, No Drawings

BORANE-SULFIDE HYDROBORATION AGENTS

BACKGROUND OF THE INVENTION

1. Field of Invention

The present invention provides a novel class of borane-sulfide hydroboration agents, their methods of production and their use in the hydroboration and reduction of organic compounds. More particularly, this invention provides novel borane dialkyl and alkoxyalkyl sulfides which have a number of advantages over the presently available agents.

2. Prior Art

Borane-tetrahydrofuran is a valuable reagent for the hydroboration of olefins and for the reduction of organic compounds. It suffers from the disadvantage in that the solutions are unstable over a period of time. U.S. Pat. No. 3,882,037 discloses stabilized borane-tetrahydrofuran solutions which permit storage of such solutions for relatively longer periods of time. However, the inherent availability only as a relatively dilute solution in tetrahydrofuran poses a serious drawback to the commercial use of this reagent.

Borane-methyl sulfide (BMS) is much more stable than borane-tetrahydrofuran and is widely used for both hydroboration and reduction [See Burg et al., *J. Am. Chem. Soc.* 76, 3307 (1954) and Coyle et al., *J. Am. Chem. Soc.* 81, 2989 (1959)]. However, it suffers from the serious disadvantage in that it yields a product which contains free dimethyl sulfide. The free dimethyl sulfide is highly volatile, b.p. 38° C., flammable and has a very noxious odor. Moreover, it is not soluble in water, so it cannot be disposed of by washing it away with water.

Borane-1,4-thioxane (U.S. Pat. No. 4,298,750) is another valuable hydroboration agent. It has both lower volatility and milder odor than dimethyl sulfide. It has a limited solubility in water and can be easily oxidized to the corresponding sulfoxide, which is miscible in water. This agent is a liquid, 8M in $BH_3$, stable over prolonged periods. Unfortunately, this commercially available reagent is relatively costly compared to borane-tetrahydrofuran and borane-dimethyl sulfide. The growing importance of borane reagents for the synthesis of pharmaceuticals and other compounds and the problems associated with other well established borane adduct hydroboration agents, e.g., low concentration and stability, high volatility, flammability, unpleasant odor, as discussed above, create a need for easy to handle, stable and environmentally benign hydroborating agents as discussed specifically below.

Thus, the search continues for effective, versatile borane-sulfide derivatives which are as effective as the commercially available reagents but which overcome the disadvantages of noxious odor, expense, volatility, and lack of water solubility. The present invention fulfills this longstanding need.

SUMMARY OF THE DISCLOSURE

The present invention provides novel borane-sulfides represented by the formula $$H_3B \cdot SR^1R^2$$

wherein B is boron, H is hydrogen, $R^1$ and $R^2$ each are straight or branched chain alkyl or alkoxy having from 1 to 5 carbon atoms with at least one R being a branched chain when both $R^1$ and $R^2$ are alkyl, and S is sulfur. When both $R^1$ and $R^2$ are alkyl, it is preferred that at least one R be isoamyl.

Representative compounds of the present invention include borane-ethylisoamyl sulfide, borane-isoamylmethyl sulfide, borane tert-butylisoamyl sulfide, borane-bis(2-methoxyethyl)sulfide, etc.

The compounds of this invention are valuable hydroborating agents. They can be prepared as the neat reagents, similar to borane-methyl sulfide, so they can be used in a range of solvents. They possess a more agreeable odor than prior art agents, yet possess hydroboration characteristics which are as effective as those of borane thioxane which is much more expensive. It is a disadvantage of borane-tetrahydrofuran that it is commercially available only as a dilute solution, 1M in tetrahydrofuran, a solution which contains 11 moles of tetrahydrofuran per mole of borane. Borane-tetrahydrofuran cannot be used conveniently in solvents other than tetrahydrofuran.

A major advantage of the reagents of this invention is the much lower volatility of the dialkyl sulfide component. Methyl sulfide has a b.p. of 38° and is highly flammable. The present dialkyl sulfides are much less volatile and constitute a much lower hazard. The odor of methyl sulfide is highly obnoxious, best charaterized as a stench. Manufacturing chemists are reluctant to use it in large scale manufacturing processes. The present dialkyl sulfides possess relatively slight odors, and odors in some cases that are quite pleasant. Consequently, they eliminate this factor from the decision of whether borane reagents should be used in large scale manufacturing processes.

The hydroborating characteristics of the present reagents are as effective as those of borane-thioxane, but their costs are considerably lower. These represent major advantages over the prior art.

In the practice of the present invention, diisoamyl sulfide was prepared in high yields (90%) by the reaction of isoamyl bromide with an aqueous solution of sodium sulfide in the presence of a phase transfer catalyst. This reaction is represented by equation I.

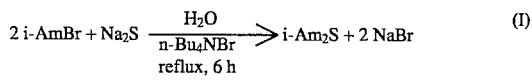

(I)

The product is isolated by simple distillation in >99% purity. It has an agreeable, mild, ethereal aroma and low volatility and is a preferred compound of the invention.

The mixed isoamyl alkyl sulfides were prepared in high yields by a routine methodology described by: (a) Reid, E. E. *Organic Chemistry of Bivalent Sulfur*, Chem. Publ. Co.: New York, 1960; Vol II, p. 24; (b) Barrett, G. C. in *Comprehensive Organic Chemistry*; Barton, D. H. R. et al., Eds., Permagon Press: Oxford, 1979, Vol. 3, p. 33; and (c) Gundermann, K. D. et al., in *Houben-Weyl Methoden der Organische Chemie*; Klamann, D., Ed.; G. Thieme: Stuttgart, 1985, Vol. 11E, p. 158. The illustrative reaction is represented by equation II.

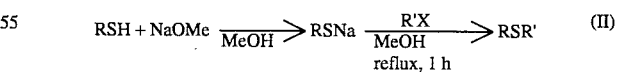

(II)

R=Et, t-Bu, i-Am

R'X=i-AmBr, MeI

Bis(2-methoxyethyl)sulfide was prepared from inexpensive thiodiethanol in an improved yield following the method described by Richter, F. et al., *J. Am. Chem. Soc.* 1952, 74, 4076. The product is isolated by simple distillation and the unreacted starting material can be recycled. In the practice of the invention, diborane was generated by treating a 2M solution of sodium borohydride with an equivalent amount of boron-trifluoride-triglyme. Diborane is readily generated as represented by reaction scheme III.

$$3NaBH_4 + 4BF_3.TG \rightarrow 2B_2H_6 + 3NaBF_4 \quad (III)$$

The $NaBF_4$ is soluble in diglyme or triglyme. The diborane (=2 $BH_3$) is passed into the desired aniline base (i.e. compounds 1 a–c or 2 a–d) being maintained at 0° C. with an external ice bath. The diborane is readily absorbed in most cases to give the borane addition compounds of the invention. This process is represented by reaction scheme IV.

$$2SRR' + B_2H_6 \rightarrow 2H_3B.SRR' \quad (IV)$$

Following the reaction, a minute sample was removed with a hypodermic syringe and passed into the standard hydrolyzing mixture. In most cases, a quantitative yield was obtained.

The flask containing the borane adduct was allowed to warm to room temperature. The escape of diborane through the bubbler was noted. Then both the borane-dialkyl sulfide and the borane-THF products were examined for borane content by removing small samples and analyzing them by hydrolysis.

The molarity of the borane in the sulfide was noted. In general, with rare exceptions, such as when R and R' are isobutyl, the content represents a quantitative transfer. A sample of each representative compound prepared was then transferred to the NMR tube and the $^{11}B$ spectrum determined.

A sample of the borane-sulfide was then mixed with 3 equivalents of 1-octene and the time noted for complete conversion to n-octylborane. Reaction scheme V represents the later steps.

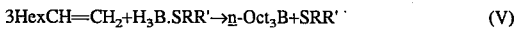

$$3HexCH=CH_2 + H_3B.SRR' \rightarrow n\text{-}Oct_3B + SRR' \quad (V)$$

Oxidation with alkaline hydrogen peroxide, a quantitative reaction, gives 94% 1-octanol and 6% of 2-octanol.

A sample of the sulfide was also mixed with an equal number of moles of borane-methyl sulfide. The $^{11}B$ spectrum revealed the formation of an equilibrium mixture of two compounds represented in reaction scheme (VI).

$$H_3B.SMe_2 + SRR' \rightleftharpoons H_3B.SMe_2 + SMe_2 + H_3B.SRR' + SRR' \quad (VI)$$

The compounds were also prepared independently by equilibrating with borane-methyl sulfide and with borane-tetrahydrofuran. Analysis of samples by hydrolysis established the presence of a 1:1 combination of the amine and the borane. Finally, each mole of borane-sulfide, with rare exceptions as indicated, hydroborated 3 moles of 1-octene.

Hydroboration of internal olefins such as 3-hexene, cyclopentene, cyclohexene, cyclooctene, and norbornene all react quantitatively in the ratio shown in reaction scheme VII.

$$3Olefin + H_3B.SRR' \rightarrow R_3B + SRR' \quad (VII)$$

Hydroboration of trisubstituted olefins, such as 2-methyl-2-butene, 1-methylcyclohexene, α-pinene, etc. proceeds in the ratio shown in reaction scheme VIII.

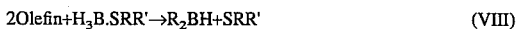

$$2Olefin + H_3B.SRR' \rightarrow R_2BH + SRR' \quad (VIII)$$

Hydroboration of more hindered alkenes, such as 2,3-dimethyl-2-butene and 2,4,4-trimethyl-2-pentene proceeds in a ratio of 1 alkene/$H_3B.SRR'$. In these cases, the products are $RBH_2$ and $SRR'$.

In all cases, the hydroboration of alkenes parallels the earlier hydroborations of representative alkenes as described in the literature for borane-tetrahydrofuran and borane-dimethylsulfide. Thus the present invention provides hydroboration reagents which are as effective as the known agents but which do not suffer from any of their drawbacks.

Borane adducts were readily prepared by saturating the neat sulfide with diborane at 0° C. The borane adducts of the present invention are liquid above 0° with high hydride constant. Their molarities are shown in Table I. The adducts are soluble in tetrahydrofuran, diethyl ether, monoglyme, dioxane, toluene and dichloromethane, solvents typically used for hydroboration.

The dialkyl sulfide adducts of the present invention are stable over prolonged periods at room temperature. No change was observed in molarity and the $^{11}B$ NMR spectrum of borane-diisoamyl sulfide and borane-ethylisoamyl sulfide over 10 months at room temperature. The $^{11}B$ NMR spectra of borane-ether sulfide adducts showed only a single absorption (quartet) in the range −20 to −26 ppm, indicating coordination of borane with the sulfur atom.

The hydroboration of 1-octene with the adducts was carried out in tetrahydrofuran solution (1M) at room temperature following the progress of the reaction by $^{11}B$ NMR. The results are shown in Table I. The reactivity of the adducts corresponds to the complexing ability of the sulfides, the borane adducts with ether sulfides being more reactive than the dialkyl sulfide adducts. The hydroborations with the ether sulfide adducts of the present invention were practically instantaneous, which is an unexpected result. The $^{11}B$ NMR spectrum taken in 5 min. showed complete transformation of 1-octene into trioctylborane. The adducts of the dialkyl sulfides required 10–15 minutes to complete hydroboration. The prior art hydroboration agent, boron-dimethyl sulfide (BMS) reaction took 45 minutes to complete.

Hydroborations on a preparative scale were carried out with borane-diisoamyl sulfide and borane-bis(2-methoxyethyl) sulfide for illustrative purposes. Thus (−)-β-pinene (93% ee) was reacted with borane-diisoamyl sulfide and the organoborane intermediate was oxidized with standard 30% hydrogen peroxide and 3M sodium hydroxide used in excess to suppress oxidation of the sulfide. (−)-cis-Myrtanol was isolated by distillation in 82% yield and the sulfide was recovered.

A representative hydroboration of 1-octene with borane-bis(2-methoxyethyl)sulfide was carried out in dichloromethane. The sulfide could not be completely removed from the organic phase by several washings with water. It was oxidized to the corresponding sulfoxide with 5% aqueous sodium hypochlorite solution. $^1H$ and $^{11}B$ NMR spectra taken after removing the solvent showed only trioctylborane isolated in 96% yield. The organoborane was oxidized with standard hydrogen peroxide/sodium hydroxide to give a mixture of 1- and 2-octanol (94:6); 94% yield.

(+)-2-Carene (99% ee) was hydroborated with borane-bis-(2-methoxyethyl)sulfide in THF at room temperature. A white precipitate of diisocaranylborane was formed in a few minutes after mixing of the reagents. It can be filtered off at this stage. Oxidation of the organoborane with hydrogen peroxide/sodium hydroxide and distillation gave a mixture of (−)-2isocaranol and the sulfide which was removed by oxidation with 5% aqueous sodium hypochlorite. (−)-2-Isocaranol (99% ee) was obtained in 81% yield.

The complexing ability of sulfides toward borane decreases in the order: dimethyl sulfide> dialkyl sulfides> ether sulfides> thioanisole. The reactivity of the corresponding borane adducts toward 1-octene, for example, increases in the same order. The dialkyl and ether borane adducts of this invention are liquids of high hydride content, stable over prolonged periods.

Diisoamyl sulfide is a particularly preferred, borane carrier. Its synthesis is simple and economical and it has an agreeable, mild, ethereal aroma. Bis(2-methoxyethyl) sulfide is also a preferred borane carrier and can be used as a cheaper alternative to 1,4-thioxane for borane complexation.

DETAILED DESCRIPTION OF PREFERRED EMBODIMENTS

The following examples further illustrate the present invention.

All glassware was oven-dried for several hours, assembled while hot and cooled in a stream of dry nitrogen gas. Syringes were assembled and fitted with needles while hot. Techniques for handling air-sensitive compounds were carried out under nitrogen atmosphere. $^1$H and $^{11}$B NMR spectra were recorded on a Varian Gemini 300 multinuclear instrument. The $^{11}$B chemical shifts are δ relative to $BF_3 \cdot OEt_2$. Optical rotations were measured on a Rudolph automatic polarimeter Autopol III. GC analyses were carried out on a Varian 3300 chromatograph (catharometer) using a 12 ft × 0.125 in column packed with 10% Carbowax 20M or SE-30 polyethylene glycol (Union Carbide) on Chromosorb W 100–120 mesh). Microanalysis were performed at the Microanalytical Laboratory, Purdue University, West Lafayette, Ind., USA.

Borane-methyl sulfide (BMS), tetrahydrothiophene, pentamethylene sulfide, dimethyl sulfide, thioanisole, 1,4-thioxane and thiodiethanol were purchased from Aldrich Chemical Company, Milwaukee, Wis. Tetrahydrofuran was freshly distilled from benzophenone ketyl prior to use. (+)-2-Carene (Camphor & Allied Products, Bombay), $[\alpha]^{23}D=+92°$ (neat) and (−)-β-pinene (Glidden Organic), $[\alpha]^{23}D=-20.8°$ (neat) were distilled prior to use from a small amount of $LiAlH_4$ under vacuum. Boron trifluoride diethyl etherate was distilled from calcium hydride under vacuum. Diglyme was distilled from a small amount of lithium aluminum hydride under vacuum.

EXAMPLE 1

Isoamylmethyl Sulfide

Sodium methoxide (5.90 g., 0.11 mol) was dissolved in methanol (50 ml). Isoamyl mercaptan (10.42 g, 0.10 mol) was added and the mixture left at room temperature for 1 hour. Methyl iodide (15.61 g, 0.11 mol) was added and the mixture was refluxed for 2 hours. Water (200 ml) was added and the mixture was extracted with pentane (2×50 ml). The extracts were combined and dried over anhydrous magnesium sulfate. The product was isolated by distillation and redistilled from lithium aluminum hydride, 10.64 g, bp 54°–55° C./35 mm Hg, 90%, $n^{20}D=1.4465$; $^1$H NMR ($CDCl_3$) δ 9.05 (d,J=6 Hz, 6H, $CH_3$), 1.47 (q,J=6 Hz, 2H, $CH_2$), 1.67 (septet, J=6 Hz, 1H, CH), 2.09, (s, 3H, $CH_3$), 2.49 (t,J=6 Hz, 2H, $CH_2$).

EXAMPLE 2

Ethylisoamyl Sulfide

Ethylisoamyl sulfide was prepared from isoamyl bromide and ethyl mercaptan according to the method of Example 1. Yield 75%, bp 54°–55° C./15 mm Hg, $n^{20}D=1.4488$; $^1$H NMR ($CDCl_3$) δ 0.92 (d,J=6 Hz, 6H, $CH_3$), 1.25 (t, J =6 Hz, 2H, $CH_2$), 1.47 (q, J=6 Hz, 2H, $CH_2$), 1.67 (septet, J=6 Hz, 1H, CH), 2.54 (J =6 Hz, 2H, $CH_2$).

EXAMPLE 3 tert-Butylisoamyl Sulfide

The title compound was prepared from isoamyl bromide and tert-butyl mercaptan according to the method of Example 1, 86% yield, bp 55°–56° C./7 mm Hg, $n^{20}D=$ 1.4460; $^1$H NMR ($CDCl_3$) δ 0.92 (d, J=6 Hz, 6H, $CH_3$), 1.32 (s, 9H, $CH_3$), 1.45 (q, 2H, $CH_2$), 1.68 (septet, 1H, CH), 2.52 (t, J =6 Hz, 2H, $CH_2$).

EXAMPLE 4

Diisoamyl Sulfide

Isoamyl bromide (21.88 g, 0.21 mol) and tetrabutylammonium bromide (1.61 g, 5 mmol) were added to a solution of sodium sulfide nonahydrate (24.02 g, 0.10 mol) in water (50 ml) and the mixture was refluxed with stirring for 6 h. The organic layer was separated, the aqueous layer was extracted with pentane (25 ml). The extract was combined with the organic layer and dried with anhydrous magnesium sulfate. Distillation gave 15.85 g, 91% of a colorless liquid, bp 49°–50° C./0.1 mm Hg, $n^{20}D=1.4514$, >99% GC pure; $^1$H NMR ($CDCl_3$) δ 0.95 (d, J=6 Hz, 12H, $CH_3$), 1.47 (q, J=6 Hz, 4H, $CH_2$), 1.68 (septet, J=6 Hz, 2H, CH), 2.51 (t, J=6 Hz, 4H, $CH_2$).

EXAMPLE 5

Bis(2-methoxyethyl) Sulfide

A solution of thiodiethanol (12.22 g, 0.1 mol) and p-toluenesulfonic acid monohydrate (0.95 g, 5 mmol) in methanol (12.82 g, 0.4 mol) was heated for 10 h at 150° C. in an autoclave provided with a glass liner. The product was isolated by distillation, 9.91 g, 66% yield, bp 55°–56° C./0.1 mm Hg, $n^{20}D=1.4609$; $^1$H NMR ($CDCl_3$) δ 2.75 (t,J=6 Hz, 4H, $CH_2$), 3.37 (s, 6H, $CH_3$), 3.57(t, J=6 Hz, 4H, $CH_2$).

EXAMPLE 6

Generation of Diborane

A 50-ml one-neck, round-bottom flask provided with a septum inlet, magnetic stirring bar and an adapter with a stopcock was charged with boron trifluoride-diglyme or -triglyme adduct (75 mmol). A 2M solution of sodium borohydride in triglyme (28.5 ml, 57 mmol) was added dropwise by means of a hypodermic syringe. Generation of diborane is smooth and the reaction is not exothermic. After the addition was completed, the flask was heated to 100° C. and kept at this temperature for 15 min. Diborane was absorbed in tetrahydrofuran (30 ml) at 0° C. Analysis of the $BH_3 \cdot$THF solution obtained for active hydride according to a standard procedure described in Brown, H. C., *Organic Syntheses via Boranes*; J. Wiley: New York, 1975, p. 241, showed 2.37M concentration of borane (95% yield); $^{11}$B NMR, δ, +1.0 ppm.

EXAMPLE 7

Preparation of Borane-Diisoamyl Sulfide

Diborane generated as described in Example 6 was passed through a bubbler containing sodium borohydride (0.1 g) in diglyme (5 ml) and a trap cooled to −78° C. was absorbed in neat diisoamyl sulfide (8.67 g, 50 mmol) at 0° C. Excess diborane was absorbed in the next bubbler containing tetrahydrofuran (10 ml) over mercury and cooled in ice water. A mercury bubbler was connected to the exit. Diborane was passed into the sulfide until the concentration of borane in THF reached 1M. Borane-diisoamyl sulfide, a colorless liquid, was stirred overnight at room temperature prior to disconnecting the bubblers and then analyzed for active hydride by a standard procedure using a water-glycerol-methanol 1:1:1 hydrolyzing mixture. Concentration 4.2M, $^{11}$B NMR, δ, −22.5 ppm.

EXAMPLE 8

Borane-Isoamyl Methyl Sulfide

Borane-isoamyl methyl sulfide was prepared by the method of Example 7 by substituting isoamyl methyl sulfide for diisoamyl sulfide.

EXAMPLE 9

Borane-Isoamyl Ethyl Sulfide

Borane-isoamyl ethyl sulfide was prepared by the method of Example 7 by substituting isoamyl ethyl sulfide for diisoamyl sulfide.

EXAMPLE 10

Borane-Isoamyl-Tert-Butyl Sulfide

Borane-isoamyl-tert-butyl sulfide was prepared by the method of Example 7 by substituting isoamyl-t-butyl sulfide for diisoamyl sulfide.

EXAMPLE 11

Borane-Bis(2-methoxyethyl)Sulfide

Borane-bis(2-methoxyethyl)sulfide was prepared by the method of Example 7 by substituting bis(2-methoxyethyl) sulfide for diisoamyl sulfide.

EXAMPLE 12

Preparation of (−)-Cis-Myrtanol

Borane-diisoamyl sulfide (5.0 ml, 21 mmol) was dissolved in THF (20 ml) and (−)-β-pinene (8.86 g, 64 mmol), $[\alpha]^{23}D=-20.8°$ (neat), 91% ee, was added at 0° C. The mixture was kept at room temperature for 1 h and oxidized by the addition of 3M sodium hydroxide (10 ml, 30 mmol) and 30% hydrogen peroxide (7 ml, 70 mmol) keeping the temperature during the addition below 30° C. and then stirring at room temperature for 3 h. The mixture was saturated with potassium carbonate, the THF layer was separated and the aqueous layer was extracted with diethyl ether (2×50 ml). The extracts were combined with the THF solution, dried over magnesium sulfate and distilled using a Widmer column to give a first fraction, 4.25 g, bp 45°–58° C./0.1 mm Hg composed of diisoamyl sulfide (77%) and cis-myrtanol (23%) and a second fraction 7.96 g (82%), bp 58°–60° C./0.1 mm Hg, $n^{20}D=1.4907$, $[\alpha]^\circ D=-19.4°$ (neat).

EXAMPLE 13

Preparation of Trioctylborane

Borane bis(2-methoxyethyl) sulfide (5.0 ml, 30 mmol) was dissolved in dichloromethane (30 ml) and 1-octene (10.10 g, 90 mmol) was added dropwise with cooling to keep the temperature at 20°–25° C. The reaction was complete in 5 min as indicated by $^{11}$B NMR. The solution was vigorously stirred with water (10×20 ml), dried over magnesium sulfate and the solvent was removed under vacuum. $^{1}$H NMR spectrum showed the sulfide present. Diethyl ether (20 ml) was added, followed by 5% sodium hypochlorite solution (40 ml) and the mixture was stirred keeping the temperature at 20°–25° C. After 1 h, the organic phase was separated, washed with water (3×20 ml) and dried over magnesium sulfate. Ether was removed under vacuum to give trioctylborane, 9.84 g, 94%, $^{11}$B NMR, δ, 86 ppm. $^{1}$H NMR did not indicate bis(2-methoxyethyl)sulfide. Tetrahydrofuran (30 ml) was added, followed by 3M sodium hydroxide (10 ml, 30 mmol) and 30% hydrogen peroxide (10 ml, 100 mmol). The mixture was stirred for 2 h at room temperature and then 1 hour at 40° C., saturated with potassium carbonate, the organic layer was separated and the aqueous layer was extracted with diethyl ether (2×30 ml). The extracts were combined with the THF solution, dried over magnesium sulfate and octanol was isolated by distillation, 10.60 g, 90.5%, bp 99°–100° C./20 mm Hg. GC analysis (Carbowax 20 M) showed 1-octanol (94%) and 2-octanol (6%).

EXAMPLE 14

Preparation of (−)-2-Isocaranol (+)-2-Carene (14.96 g, 0.11 mol), $[\alpha]^{23}D+92°$ (neat), was added to a solution of borane-bis(2-methoxyethyl)sulfide (8.2 ml, 50 mmol) in tetrahydrofuran (50 ml) at 10°–20° C. A white precipitate formed in 5 min. $^{11}$B NMR showed no borane signal and only a signal at δ, 31.1 ppm. After 1 hour, water (2 ml) was added and the organoborane was oxidized under nitrogen by the addition of 3M sodium hydroxide (30 ml, 90 mmol) and 30% hydrogen peroxide (12 ml, 120 mmol) at 20°–30° C., stirred for 2 h and then for 1 h at 40° C. The mixture was saturated with potassium carbonate, the organic phase was separated and the aqueous phase was extracted with diethyl ether (2×50 ml). The extracts were combined with the THF solution, washed with saturated brine (10 ml) and dried over magnesium sulfate. Distillation gave a mixture of bis(2-methoxyethyl)sulfide and (−)-2-isocaranol. The distillate was dissolved in diethyl ether (25 ml) and added dropwise with vigorous stirring to a 5% aqueous sodium hypochlorite solution (80 ml) at 20°–25° C. After 1 h, the organic solution was separated, the aqueous solution was extracted with diethyl ether (25 ml), the extract was combined with the organic solution, dried over magnesium sulfate and distilled to give 12.52 g (81%) of (−)-2-isocaranol, bp 50°–52° C./0.05 mm Hg, $[\alpha]_{23}D=-31°$ (neat).

The properties of representative borane alkyl and ether sulfides of the present invention and commercial prior art agents are summarized in Tables I and II.

TABLE I

| sulfide | exchange with BMS[1] | borane adduct [BH₃][2] M | ¹¹B NMR δ, ppm[4] | hydroboration[3] min |
|---|---|---|---|---|
| dimethyl sulfide | | 10.0 | −20.3 | 45 |
| isoamylmethyl sulfide | 46 | 5.8 | −21.3 | 10 |
| tert-butylmethyl sulfide | 39 | 6.6 | −24.6 | 10 |
| ethylisoamyl sulfide | 44 | 5.2 | −23.1 | 10 |
| tert-butylisoamyl sulfide | 32 | 4.3 | −25.9 | 10 |
| diisoamyl sulfide | 40 | 4.2 | −22.5 | 15 |
| tetrahydrothiophene | 46[5] | 8.1 | −20.6 | 15 |
| pentamethylene sulfide | 45 | 7.5 | −22.8 | 15 |
| 3-ethylthiotetrahydrofuran | 21 | 5.8 | −24.5 | 5 |
| bis(2-methoxyethyl) sulfide | 16 | 6.0 | −22.6 | 5 |
| 1,4-thioxane | 17 | 8.0 | −23.0 | 5 |
| bis(3-tetrahydrofuryl sulfide | 0 | 4.6 | −26.0 | 5 |
| thioanisole | 0[6] | 3.0 | −20.6 | |

[1]BMS and sulfide mixed at 1:1 molar ratio.
[2]Estimated by hydrolysis in water-glycerol-methanol 1:1:1, and measuring hydrogen evolved.
[3]Hydroboration of 1-octane in THF at 20–25° C. Concentration of the adduct 1 M.
[4]Neat.
[5]Calculated from the exchange with boran-tert-butylmethyl sulfide.
[6]Unstable over longer periods.

TABLE II

Relative Odors of Borane Adducts with Organic Sulfides

| sulfide | odor |
|---|---|
| dimethyl sulfide | stench |
| isoamylmethyl sulfide | ethereal, strong |
| tert-butylmethyl sulfide | stench |
| ethyliosamyl sulfide | etheral, strong |
| tert-butylisoamyl sulfide | ethereal, mild |
| diisoamyl sulfide | ethereal, mild, agreeable |
| tetrahydrothiophene | stench |
| pentamethylene sulfide | stench |
| 3-ethylthiotetrahydrofuran | stench |
| bis(2-methoxyethyl) sulfide | mild |
| 1,4-thioxane | mild |
| bis(3-tetrahydrofuryl sulfide | stench |
| thioanisole | stench |

The invention claimed is:

1. A borane-sulfide represented by the formula $$H_3B.SR^1R^2$$

wherein B is boron, H is hydrogen, R¹ is a straight or branched chain alkyl or alkoxy group having from 1 to 5 carbon atoms, R² is a straight or branched chain alkyl or alkoxy group having from 1 to 5 carbon atoms with the limitation that at least one R group must be a C3–C5 branched chain alkyl when the other is straight chain alkyl, and S is sulfur.

2. A compound of claim 1 wherein R¹ is isoamyl.
3. A compound of claim 2 wherein R² is ethyl.
4. A compound of claim 2 wherein R² is isoamyl.
5. A compound of claim 2 wherein R² is methyl.
6. A compound of claim 2 wherein R² is tert-butyl.
7. A compound of claim 1 wherein R¹ is alkoxy.
8. A compound of claim 7 wherein both R¹ and R² are methoxyethyl.
9. A compound in accordance with claim 1, borane-diisoamyl sulfide.
10. A compound in accordance with claim 1, borane-isoamyl methyl sulfide.
11. A compound in accordance with claim 1, borane-isoamyl ethyl sulfide.
12. A compound in accordance with claim 1, borane-isoamyl-tert-butyl sulfide.
13. A compound in accordance with claim 1, borane-bis(2-methoxyethyl) sulfide.

* * * * *